United States Patent
Speldrich et al.

(10) Patent No.: US 6,904,907 B2
(45) Date of Patent: Jun. 14, 2005

(54) INDIRECT FLOW MEASUREMENT THROUGH A BREATH-OPERATED INHALER

(75) Inventors: Jamie W. Speldrich, Freeport, IL (US); Martin G. Murray, Freeport, IL (US); Richard Gehman, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 149 days.

(21) Appl. No.: 10/300,442

(22) Filed: Nov. 19, 2002

(65) Prior Publication Data

US 2004/0094151 A1 May 20, 2004

(51) Int. Cl.[7] .............................................. A61M 11/00
(52) U.S. Cl. .............................. 128/200.23; 128/200.14
(58) Field of Search ........................ 128/200.23, 200.22, 128/203.23, 204.22, 202.22, 203.12, 200.14

(56) References Cited

U.S. PATENT DOCUMENTS

| | | | |
|---|---|---|---|
| 4,130,116 A | * 12/1978 | Cavazza ................. | 128/200.23 |
| 5,450,336 A | 9/1995 | Rubsamen et al. | |
| 5,469,750 A | 11/1995 | Lloyd et al. | |
| 5,622,162 A | 4/1997 | Johansson et al. | |
| 5,743,252 A | 4/1998 | Rubsamen et al. | |
| 5,755,218 A | 5/1998 | Johansson et al. | |
| 6,105,575 A | 8/2000 | Estes et al. | |
| 6,260,549 B1 | * 7/2001 | Sosiak .................... | 128/200.23 |
| 6,263,872 B1 | * 7/2001 | Schuster et al. ....... | 128/203.26 |
| 6,390,088 B1 | * 5/2002 | Nohl et al. ............ | 128/200.23 |
| 6,629,524 B1 | * 10/2003 | Goodall et al. ........ | 128/200.14 |

* cited by examiner

*Primary Examiner*—Henry Bennett
*Assistant Examiner*—Mital Patel
(74) *Attorney, Agent, or Firm*—Kris T. Fredrick; Kermit Lopez; Luis Ortiz

(57) ABSTRACT

Indirect airflow measurement through breath-operated device is accomplished by incorporating an airflow sensor into the inhaler device along a low resistance channel disposed away from the exhaust chamber of the device and having an input port in airflow communication with a low resistance channel and output input port and low resistance channel are formed in the main housing body of the device, and further incorporating an output port formed near the exhaust changer near the mouthpiece assembly, the output port also in airflow communication with the low resistance channel. A method of measuring airflow in an inhalation device is also described that measures air flowing through the low resistance channel. Another aspect of the invention provides a method that allows for the closure of the devices' airflow ports, by allowing for the rotation of the mouthpiece assembly from open to closed positions relative to the inhaling device's main housing body and towards handle assembly.

10 Claims, 5 Drawing Sheets

INDIRECT FLOW MEASUREMENT THROUGH A BREATH-OPERATED INHALER

TECHNICAL FIELD

Figure 1:
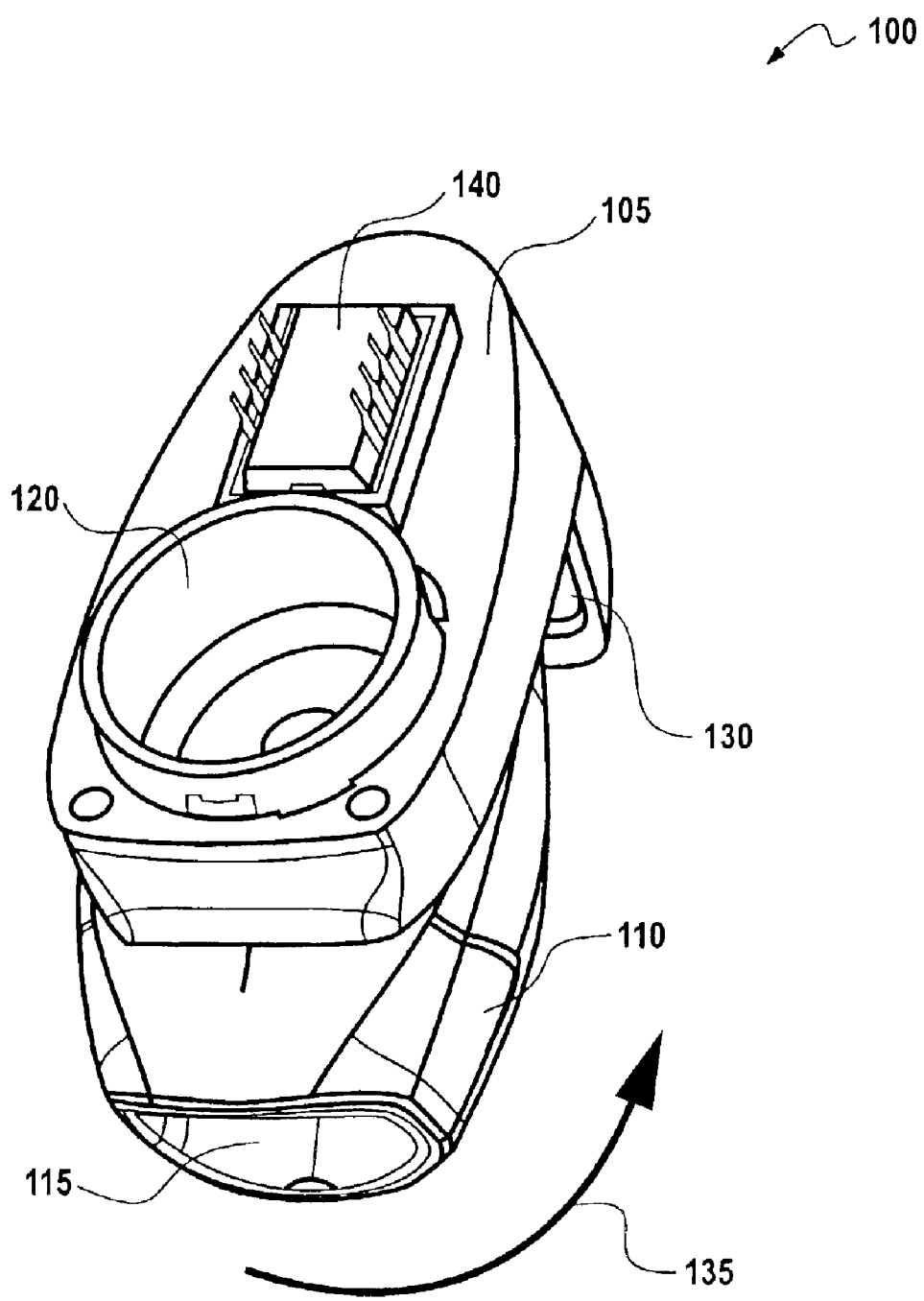

This invention relates to breath-operated inhaler devices. More particularly the present invention relates to providing indirect flow measurement through a breath-operated inhaler device. The present invention is also related to providing indirect flow measurement within and/or through an inhalation device by drawing air to an airflow sensor through a low resistance channel that is physically separated from the inhaler device's exhaust chamber. A method also provides for closure of the inhaler device airflow ports by allowing rotation of the mouthpiece assembly from open to closed positions relative to an inhaler device's main body and handle assembly.

BACKGROUND OF THE INVENTION

Devices for releasing a controlled dose of medication may be actuated electronically. Such devices are generally referred to as inhalers, inhaling devices, breath inhaling devices, and breath-operated inhaling devices. Historically, the patient actuates inhalers mechanically as he or she inhales. Difficulty arises for many patients in coordinating breathing and actuating the medicine delivery. Newer devices in development can now deliver medicine automatically and more precisely by measuring the flow rate and triggering the actuator as the patient inhales. At a certain flow rate, the lung passages are detected as open and the output of a sensor may be fed back to a comparator or microprocessor to actuate medicine delivery. To trigger such a device, either a pressure sensor or a flow sensor generally senses flow. A pressure sensor may be ported to sense pressure drop created by flow through the mouthpiece assembly or through an orifice in the mouthpiece assembly. But with pressure sensing technology, larger diaphragms are typically needed to sense the very low pressure drop required with breath-operated devices. As a consequence, devices with the larger size diaphragm cost more.

Two types of flow sensors are regularly used to measure flow in medical equipment: a hot wire anemometer or its miniature form, the silicon-based thermal microsensor (also known as the micro-bridge airflow sensor or thermally based Micro Electronic Mechanical System (MEMS) device). A flow sensor is typically deployed by placing it directly in the flow stream; but flow sensor wire bonds or sensing elements may be damaged by debris, lint, or from patient mishandling. Hot wire anemometer flow sensors have the disadvantage of requiring relatively high power. Although thermal microsensor type flow sensors operate with lower power, flow turbulence generated within the breath-operated device and extraneous flow in ambient air cause signal errors when placed directly in the flow.

U.S. Pat. No. 5,469,750, entitled "Method and Apparatus for Sensing Flow in Two Directions and Automatic Calibration Thereof", is directed to a method of calibrating the output of a transducer in a flow path through which a medication is delivered from a hand-held metered dose inhaler. A transducer senses flow rates of human breath during inhalation and exhalation through a portion of a flow path in the inhaler. The flow rates have two non-linear flow characteristics in opposite directions. The flow path portion provides flow rate measurements representative of flow paths of the entire system. U.S. Pat. No. 5,622,162, entitled "Method and Apparatus for Releasing a Controlled Amount of Aerosol Medication Over a Selectable Time Interval", is directed to another portable, but battery powered, hand-held system for releasing a controlled dose of aerosol medication for inhalation by a patient, including a durable body and a medication cassette inserted in the durable body. The cassette includes a housing for containing a canister of medication, bears an identification code, and permits the canister to be manually depressed to release a dose, e.g., a metered dose, when out of the durable body. The durable body includes an actuator mechanism for engaging an inserted cassette and its canister and an actuator release mechanism for controlling the actuator mechanism to depress the canister for a selected period of time in order to release the desired dose of medication and then the release the canister. The actuator mechanism includes a compression spring for depressing the canister and a torsion spring for reloading the compression spring. The torsion spring is reloaded by rotating the cassette from an open position for delivering aerosol to a closed position. The actuator-release mechanism includes a motor and trigger pin assembly that controls the release of the compression spring and the torsion spring, and, hence, the time that the canister is depressed. The motor operates in response to sensed flow satisfying a selected delivery threshold. The durable body includes a flow sensor having an asymmetrical orifice that is calibrated, independent of the cassette, to convert the sensed pressure due to flow into a flow rate. The orifice is separately calibrated for an inhalation flow rate range and an exhalation flow rate range over a selected number of known flow rates. The sensed pressure value is corrected for transducer offset drift and converted to a flow rate using the calibration data and piecewise linear interpolation.

Generally, prior art inhalation device sensors sense flow through a general flow path formed in the inhalation device by using a pressure sensor to measure pressure drop or by mounting a flow sensor directly in the flow path. The present inventors have recognized that a more sensitive technique is needed. The present inventors have invented and herein describe an indirect flow sensing technique that uses flow outside of the direct flow path associated with the sensing apparatus. Airflow can instead be driven through a low resistance channel across the airflow sensor using the present invention. Such a technique is more sensitive at very low flows than the pressure sensor technology described by the prior art and more durable than having an airflow sensor mounted directly in the flow channel.

The indirect flow sensing method can also be incorporated in an inhalation device that allows for the closure of the device's airflow ports by allowing for the rotation of the mouthpiece assembly from open to closed positions relative to the inhaling device's main body and handle assembly.

Accordingly, the present invention is described and presented to address the shortcomings currently found with the prior airflow sensing art.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and the abstract as a whole. Additional objects and advantages of the current invention will become apparent to one of ordinary skill in the art upon reading the specification.

In accordance with a feature of the present invention, a flow sensor is described that allows for indirect (separate and apart from the exhaust chamber) measurement of airflow through a breath-operated device.

In accordance with another feature of the present invention, indirect air flow measurement through a breath-operated device is accomplished by incorporating a flow sensor along a low resistance channel, wherein an input port and the low resistance channel that are formed in the main body of the device separate from the device's exhaust chamber, and incorporating a output port also in communication with the low resistance channel that is formed near the exhaust chamber of the mouthpiece.

The indirect airflow measurement technique can also enable closure of the device's airflow ports by incorporating a design that allows for the rotation of the mouthpiece assembly from open to closed positions relative to the inhaling device's main housing body, including a handle assembly.

Indirect measurement of flow through a breath-operated device incorporates a flow sensor into the device and in airflow communication with a low resistance channel formed within the main body of the device together with an input port also in airflow communication with the low resistance channel. An output port is formed near the device's exhaust chamber, and preferably upstream of aerosol delivery. Both input and output ports are oriented such that the openings, which tap to the main channel, are perpendicular to the flow direction through the main channel. The output port and an aerosol delivery assembly are placed within the exhaust chamber and a low resistance channel leads from the upstream port to the sensor and then to the downstream ports. The very low-pressure drop generated by flow through the main channel mouthpiece assembly drives a small flow through the low resistance channel and across the sensor. The indirect flow measurement technique has the advantage over pressure sensor technology in that using a low resistance channel to the sensor and the high sensitivity of a thermal microsensor at low flows inherently allows it to sense very low pressure drop. A thermal microsensor can be used in the present invention to operate with low power dissipation. Furthermore, by placing the flow sensor outside the main flow path, aspects of the present invention provide for a more robust inhaling device because delicate sensing elements and wirebonds typically located within airflow sensors are physically protected.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

FIG. 1 is a front-top-side view of an inhaling device in accordance with the present invention;

FIG. 2 is a cross-section illustration of the inhaling device in accordance with the present invention;

FIG. 3 is a bottom-side-front perspective view of an inhaling device in accordance with the present invention; and FIG. 4 is a cross-sectional front-side view of an inhaling device in accordance with the present invention; and FIG. 5 is another cross-sectional front-side view of an inhaling device in accordance with the present invention showing an improved flow channel.

DETAILED DESCRIPTION OF THE INVENTION

The novel features of the present invention will become apparent to those of skill in the art upon examination of the following detailed description of the invention or can be learned by practice of the present invention. It should be understood, however, that the detailed description of the invention and the specific examples presented, while indicating certain embodiments of the present invention, are provided for illustration purposes only because various changes and modifications within the scope of the invention will become apparent to those of skill in the art from the detailed description of the invention and claims that follow. Drawings associated with the following description provide like reference numerals that refer to identical or functionally similar elements throughout separate views and are incorporated in and form part of the specification.

Referring to FIG. 1, the flow path of a breath-operated inhaler device 100 in accordance with embodiments of the present invention is incorporated into a mouthpiece assembly 110 having an exhaust port 115. The mouthpiece assembly 110 has an exhaust chamber formed by exhaust port 115 and adapted to allow a user to draw air from/through the device 100, air that can be combined with, for example, an aerosol from an aerosol canister (not shown, but generally known to be used with inhalation devices) within the exhaust chamber 113 (shown in FIG. 2). The inhaler device 100 is adapted with an aerosol canister receiver/holder/delivery assembly 120, hereinafter referred to as the aerosol canister holding and aerosol delivery assembly 120. The exhaust port 115 opening area of the mouthpiece assembly 110 can be rotated as indicated by the arrow 135 to a closed position against a handle portion 130 while not in use. Rotation would cause exhaust port 115 to be located against handle portion 130, thereby closing or sealing the exhaust port 115 opening. It should be appreciated by those skilled in the art that the flow sensing methods and systems described herein can also be applied to breath-operated inhalers that do not provide a rotating section for closure of device portals. Also indicated in FIG. 1 is an electronic device or sensor 140. The sensor 140 can be provided in the form of a thermal microsensor electro-mechanically adapted to a chip carrier for sensing and monitoring airflow through the inhaler 100.

Referring to FIG. 1, the mouthpiece 110 flow path is modified by taking a housing section 105 from the aerosol feature mouthpiece through the centerline of the assembly. This section 105 has two walls used to form a low resistance channel 230 to the sensor 140 contained in housing section 105. An input port 280 is formed behind the aerosol canister holding and aerosol delivery assembly 120 near the handle assembly 130 and an output port 220 is formed near the inlet of a main airflow channel 250 formed in the mouthpiece assembly 110. Both ports 280 and 220 are relatively large openings and shown perpendicular to air flow, connected to a low resistance channel 230.

$$Re = \frac{V * D * \rho}{\mu}$$

where

V=Velocity of flow

D=Diameter of geometry

P=Density of fluid $\mu$=Viscosity of fluid

Lowering the Reynold number in an air-flow based system will generally reduce turbulence. Lower turbulence is desirable in a flow sensor 140 since it results in less output noise. Splitting the airflow path through the center can reduce the diameter variable and, therefore, reduce output noise.

The shape of the low resistance channel 230 flow path can be provided such that flow enters the main airflow channel 250 at about a 90° angle with a large opening and reduces area as flow changes direction. This is another improvement over prior art in that previous designs requiring up to 180° change in flow direction, which can cause flow instability and pressure losses. To reduce the angle to about 90° and reduce flow eddies, the lower duct wall 260 can be reduced in length and rounded compared to prior art devices. The new flow path geometry improves control of the flow and still allows the mouthpiece assembly 110 to be rotated toward the handle assembly 130, thus enabling airflow channels associated with the mouthpiece assembly 110 and handle assembly 130 to be sealed shut.

Figure 2:
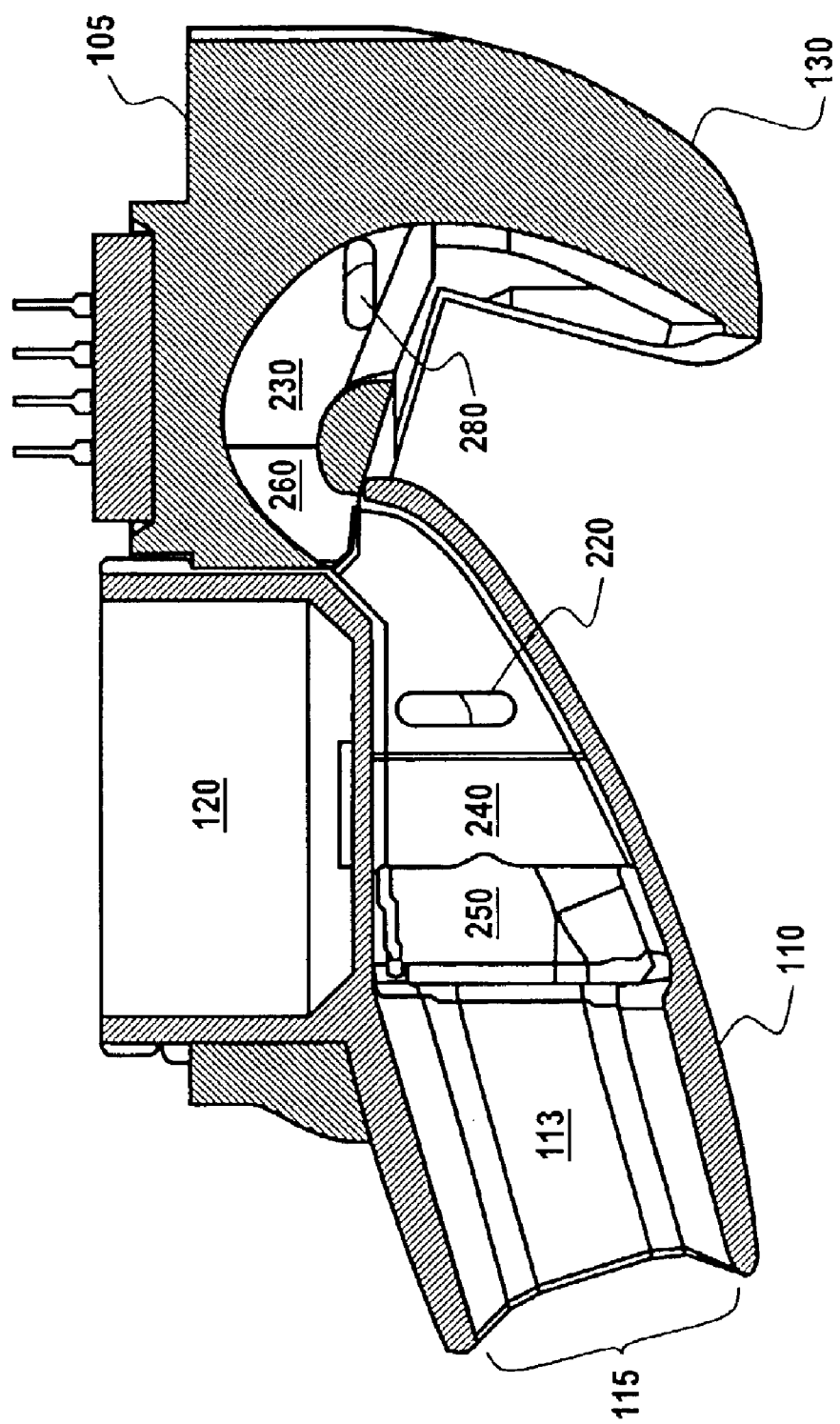
Figure 3:
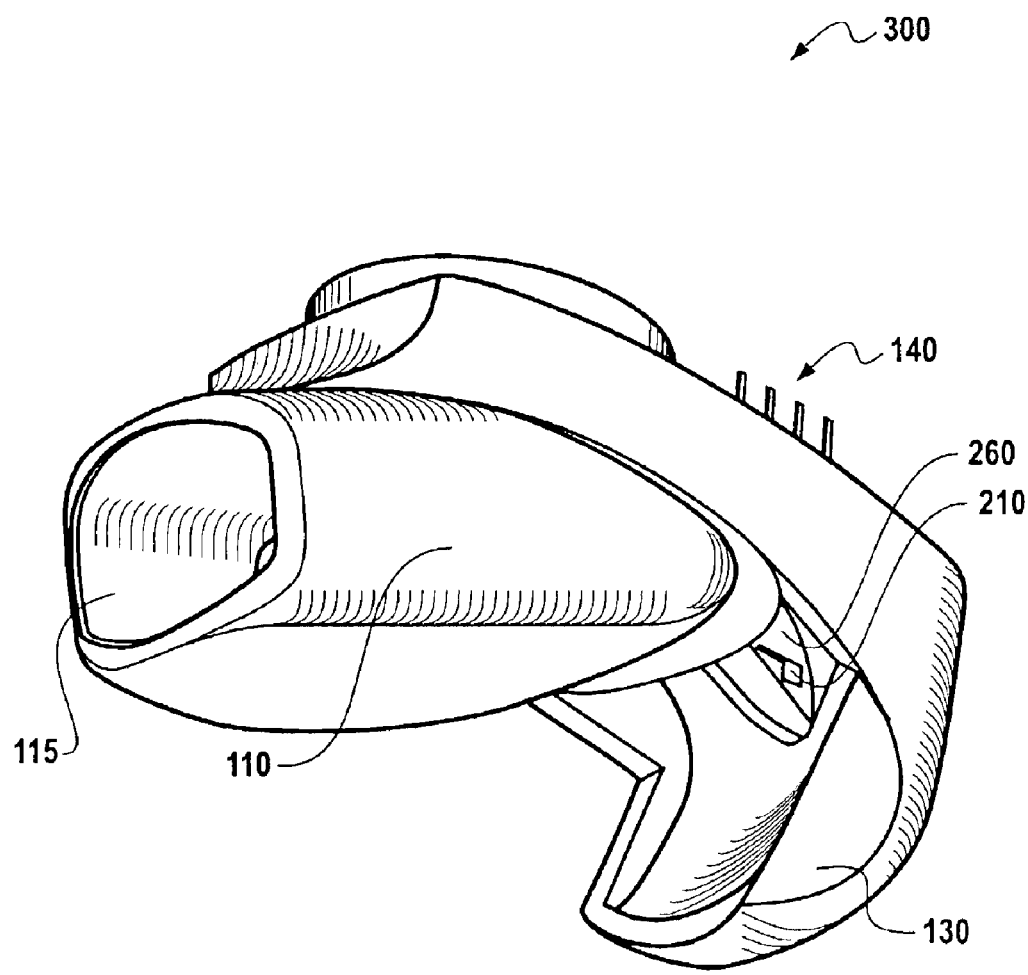
Figure 4:
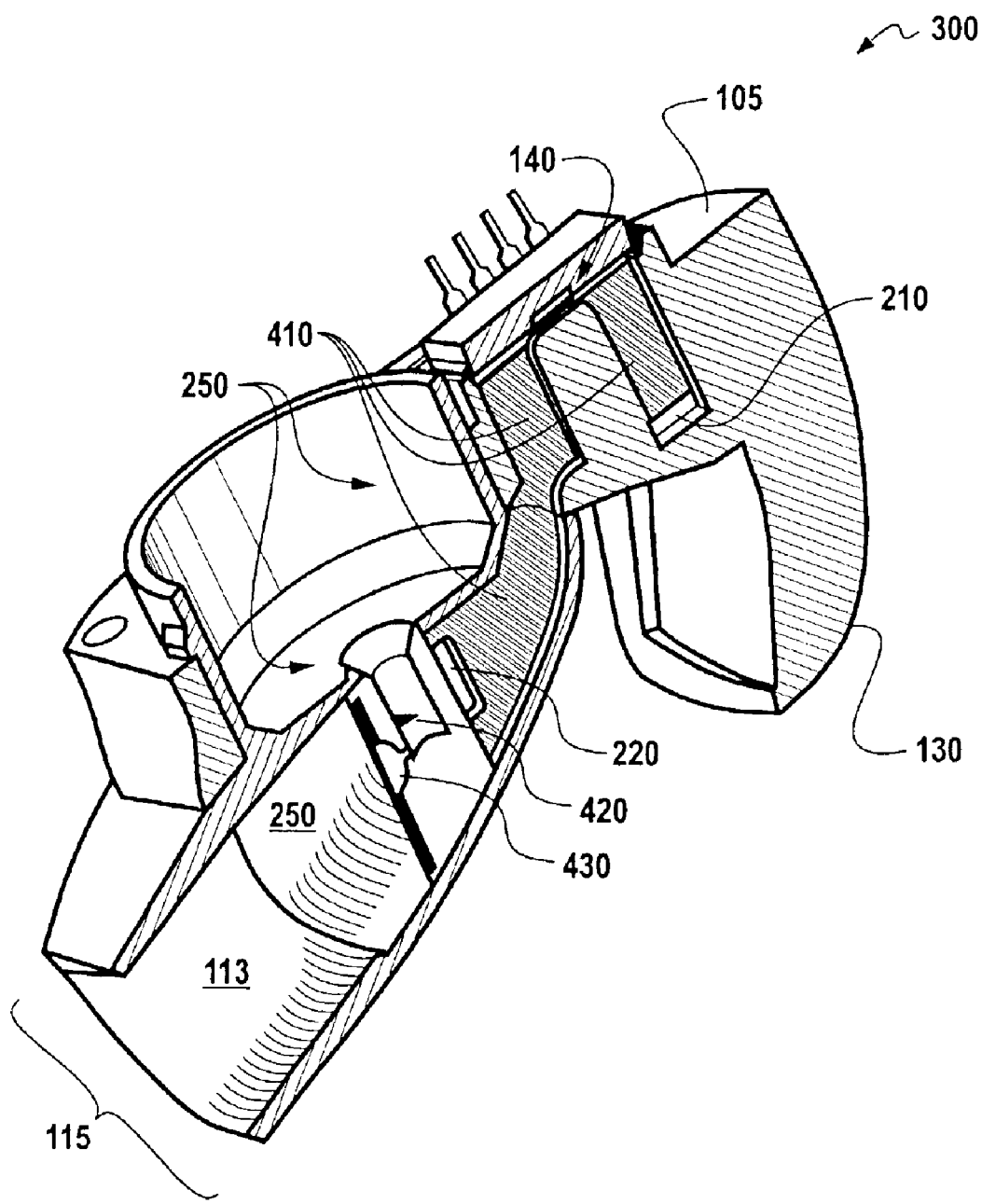

Referring to FIG. 3, a 3-point (bottom-side-front) perspective view of an inhaling device 300 in accordance with another embodiment of the present invention is shown. As shown in FIG. 3, the mouthpiece assembly 110 has an exhaust port 115 formed in it that can further define an exhaust chamber 113 (as seen in FIG. 4) within the mouthpiece assembly 110. A user is able to draw air, which may be combined with an aerosol or other agent in the exhaust chamber 113 (and/or main airflow channel 250 of FIGS. 2 and 4) through the device 300. In order to reduce flow turbulence and resulting sensor inaccuracy while a user draws airflow through the device 300, an improved flow path referred to as a low resistance channel (not shown in the figure) is provided or formed at or within the handle assembly 130. Also formed within the handle is input port 210, which operates as an inlet and allows air to flow to the sensor 140. The outer portion of a wall of low resistance associated with the low resistance channel is also shown.

Referring to FIG. 4, a cross-sectional front-side view of an inhaling device 300 as shown in FIG. 3 is illustrated. Again, sensor 140 is shown disposed on the top of the device 300. During use, inlet port 210 allows airflow to pass through a low resistance channel 410 toward the sensor 140. Output port 220 operates as an outlet for allowing air flowing through low resistance channel 410 and by airflow sensor 140 to combine with aerosol provided from an aerosol delivery zone 420 through an internal port 430 into the main airflow channel 250. Air from the sensor 140 and input port 210 can be allowed to combine with aerosol provided from an aerosol canister holding and aerosol delivery assembly 250.

Figure 5:
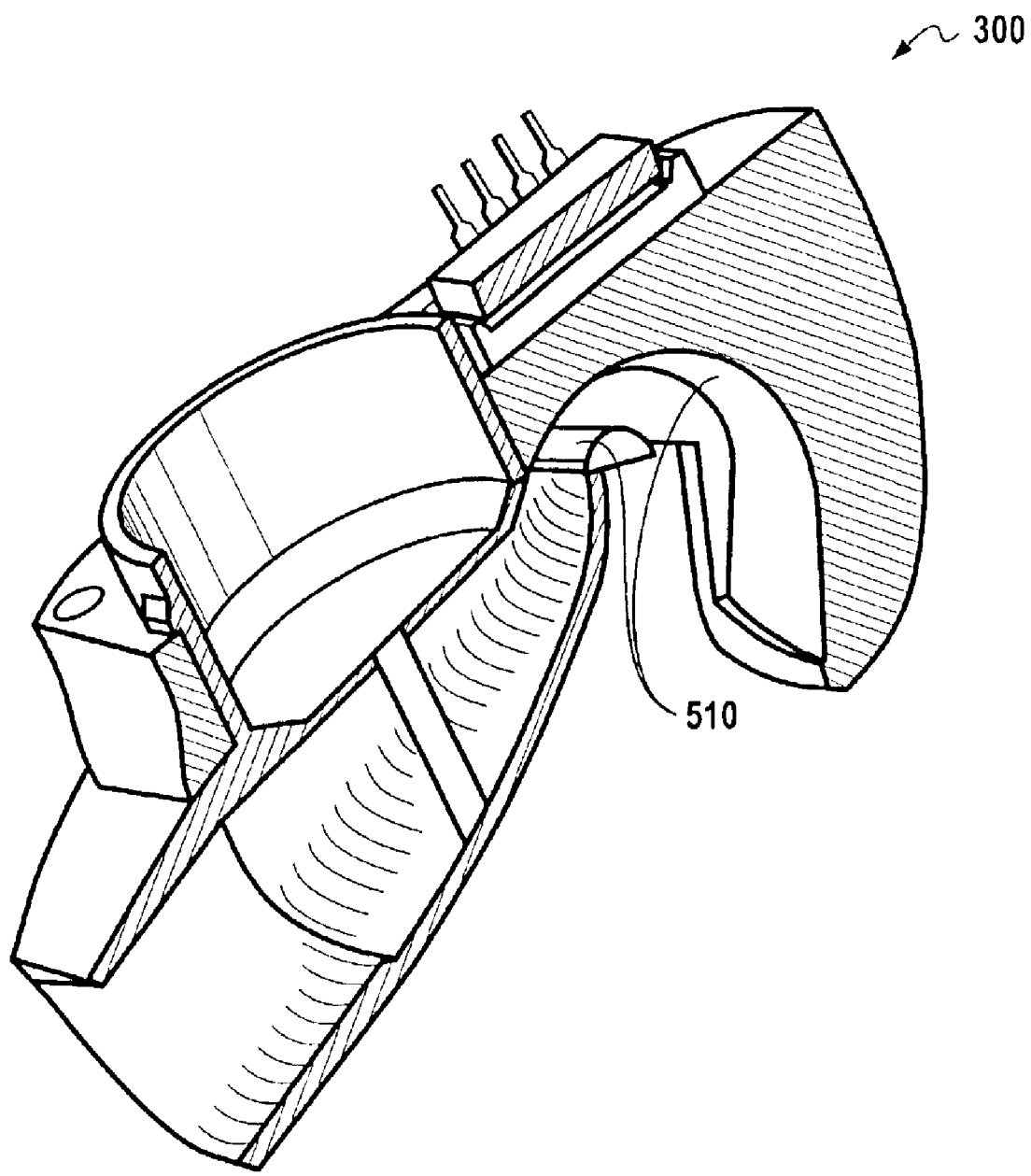

Referring to FIG. 5, another cross-sectional front-side view of an inhaling device 300 as illustrated in FIG. 3 is shown with an improved airflow channel design 510 in accordance with embodiments of the present invention.

It should be appreciated by those skilled in the art that the inhaler device described in the present specification can be formed from many materials, including plastic. Plastic is useful for injection molding manufacturing techniques and would be a less expensive material for mass production of the device. It should be appreciated, however, that the device can be made of other materials; therefore, reference to plastic or injection molding should not be taken as a limitation over the scope of the present invention.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. An inhaler device, comprising:
   a housing body including an aerosol canister holding and aerosol delivery assembly and a handle assembly, said housing body having a low resistance channel formed therein;
   a mouthpiece assembly having an exhaust port formed therein and defining an opening for an exhaust chamber, wherein said mouthpiece assembly is adapted to receive aerosol from an aerosol canister held by said aerosol canister holding and aerosol delivery assembly;
   an airflow sensor installed on said housing body and adapted to provide measurement of airflow through said low resistance channel;
   an input port in airflow communication with said airflow sensor through said low resistance channel, said input port formed to allow air to flow into said housing body through said low resistance channel; and
   an output port in airflow communication with said airflow sensor through said low resistance channel, said output port formed within said mouthpiece assembly near said exhaust port, wherein air flowing from said output port merges with aerosol provided from said aerosol canister holding and aerosol delivery assembly within said exhaust chamber;
   wherein said mouthpiece assembly is rotatable attached to said main housing such that said exhaust port of said mouthpiece assembly and said mouthpiece assembly can be rotated 180 degrees toward said handle assembly accomplishing complete closure of the input port and exhaust port.

2. The device of claim 1, wherein said airflow sensor is a thermal microsensor.

3. The device of claim 1, wherein inhaler device is formed from plastic.

4. An inhaler device, comprising:
   a housing comprising an aerosol canister holding and aerosol delivery assembly and a handle assembly, wherein said aerosol canister holding and aerosol delivery assembly and said handle assembly form said main housing body;
   a flow sensor attached to said main housing, wherein said flow sensor is adapted for carrying out indirect measurement of air flowing through said inhaler device;
   an input port in communication with said flow sensor, said input port formed in said main housing and adapted for enabling air to flow into said inhaler device; and
   a mouthpiece assembly having an exhaust port and an output port formed therein, wherein:
   said mouthpiece assembly is rotatably attached to said housing at said aerosol canister holding and aerosol delivery assembly such that said exhaust port and said mouthpiece assembly can be rotated 180 degrees toward said handle assembly for storage of said inhaler device accomplishing complete closure of the input port and exhaust port;

said mouthpiece assembly is further adapted to receive aerosol from an aerosol canister held by said aerosol canister holding and aerosol delivery assembly;

said output port is in airflow communication with said flow sensor, said output port formed within said mouthpiece assembly near said exhaust port;

air flowing from said output port can merge with aerosol from said aerosol canister holding and aerosol delivery assembly within said exhaust chamber, and air entering said inhaler device from said input port is received by said flow sensor and is discharged from said inhaler device through said exhaust port.

5. The device of claim 4, wherein said airflow sensor is provided as a silicon chip.

6. The device of claim 4, wherein said airflow sensor is provided as a thermal microsensor.

7. The device of claim 4, wherein inhaler device is formed from plastic.

8. A method of using an inhalation device, comprising the steps of:

providing an inhalation device, which further comprises a housing having a low resistance channel formed therein and including an aerosol canister holding and aerosol delivery assembly, a handle assembly, a mouthpiece assembly having an exhaust port formed therein and defining an opening for an exhaust chamber, wherein said mouthpiece assembly is adapted to receive aerosol from an aerosol canister held by said aerosol canister holding and aerosol delivery assembly, an airflow sensor incorporated within said inhaler device that allows for indirect measurement of airflow through said low resistance channel, an input port in airflow communication with said airflow sensor, said input port formed in said handle assembly, wherein air flows into said housing from said input port through said low resistance channel, and an output port formed within said mouthpiece assembly near the exhaust chamber and in airflow communication with said low resistance channel and said airflow sensor, wherein air flowing from said output port merges into air flowing from said aerosol canister holding and aerosol deliver assembly within said exhaust chamber, said mouthpiece assembly rotatabley attached to said housing at said aerosol canister holding and aerosol delivery assembly such that said exhaust port and said mouthpiece assembly can be rotated 180 degrees toward said handle assembly accomplishing complete closure at the input port and exhaust port;

rotating said mouthpiece assembly on said housing 180 degrees such that said exhaust port and said input port are opened;

drawing air through said inhalation device from said mouthpiece assembly, causing air to flow through said input port, low resistance channel, output port, exhaust chamber, and exhaust port; and sensing air flowing through said low resistance channel by said drawing step using said airflow sensor.

9. The method of claim 8, further comprising the step of:

providing aerosol from an aerosol canister held by said aerosol canister holding and aerosol deliver assembly in response to airflow sensed by said airflow sensor.

10. The method of claim 9, wherein aerosol provide from said aerosol canister held by said aerosol canister holding and aerosol delivery assembly is controlled by said airflow sensor.

* * * * *